United States Patent
Beckman (10) Patent No.: US 11,938,234 B2
(45) Date of Patent: Mar. 26, 2024

(54) VISIBLE LIGHT SANITIZING SYSTEMS AND METHODS

(71) Applicant: THE BOEING COMPANY, Chicago, IL (US)

(72) Inventor: John C. Beckman, Everett, WA (US)

(73) Assignee: The Boeing Company, Chicago, IL (US)

(*) Notice: Subject to any disclaimer, the term of this patent is extended or adjusted under 35 U.S.C. 154(b) by 588 days.

(21) Appl. No.: 16/894,935

(22) Filed: Jun. 8, 2020

(65) Prior Publication Data

US 2021/0379217 A1    Dec. 9, 2021

(51) Int. Cl.
*A61L 2/08* (2006.01)
*A61L 2/24* (2006.01)
*E03D 9/00* (2006.01)

(52) U.S. Cl.
CPC .......... *A61L 2/084* (2013.01); *A61L 2/24* (2013.01); *E03D 9/00* (2013.01); *A61L 2202/11* (2013.01); *A61L 2202/14* (2013.01)

(58) Field of Classification Search
CPC .......... A61L 2/084; A61L 2/24; E03D 9/00
See application file for complete search history.

(56) References Cited

U.S. PATENT DOCUMENTS

| | | |
|---|---|---|
| 9,783,974 B1 | 10/2017 | Tillotson |
| 2017/0246331 A1 | 8/2017 | Loyd |
| 2018/0209613 A1 | 7/2018 | Callahan |
| 2018/0311386 A1* | 11/2018 | Hawkins ............ A61L 2/24 |
| 2018/0311387 A1 | 11/2018 | Hawkins |
| 2019/0053674 A1* | 2/2019 | Hall ................ B01J 23/50 |
| 2020/0061223 A1 | 2/2020 | Hallack |
| 2020/0331611 A1* | 10/2020 | Hack ................ A61L 2/10 |

FOREIGN PATENT DOCUMENTS

WO    WO 2018/130750    7/2018

OTHER PUBLICATIONS https://vitalvio.com/the-science/.
https://www.ecmag.com/section/lighting/sanitizing-light-leds-become-disinfectant-technology.
Extended European Search Report for EP 21177995.4-1012, dated Nov. 15, 2021.
Communication for EP 21177995.4-1012, dated May 3, 2023.

* cited by examiner

Primary Examiner — Kevin Joyner
(74) Attorney, Agent, or Firm — Joseph M. Butscher; The Small Patent Law Group LLC (57) ABSTRACT

A sanitizing system and method are configured to disinfect at least one surface within an area. The sanitizing system and method include a lighting assembly configured to emit disinfecting visible light onto the at least one surface. The disinfecting visible light is configured to neutralize microorganisms on the at least one surface.

20 Claims, 8 Drawing Sheets

VISIBLE LIGHT SANITIZING SYSTEMS AND METHODS

FIELD OF THE DISCLOSURE

Embodiments of the present disclosure generally relate to sanitizing systems, such as may be used to sanitize structures and areas within vehicles, such as commercial aircraft.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

In order to sanitize a surface of a structure, a known UV light sterilization method emits a broad spectrum UVC light onto the structure. However, UVC light typically takes a significant amount of time (for example, three minutes) to kill various microbes. Further, various microbes may not be vulnerable to UVC light. That is, such microbes may be able to withstand exposure to UVC light.

Also, certain types of microbes may develop a resistance to UVC light. For example, while UVC light may initially kill certain types of microbes, with continued exposure to UVC light over time, the particular species of microbe may develop a resistance to UVC light and able to withstand UVC light exposure.

Additionally, direct exposure of certain types of UV light may pose risk to humans. For example, certain known UV systems emit UV light having a wavelength of 254 nm, which may pose a risk to humans. As such, certain known UV light disinfection systems and methods are operated in the absence of individuals. For example, a UV light disinfection system within a lavatory may be operated when no individual is within the lavatory, and deactivated when an individual is present within the lavatory.

Also, UV radiation may degrade certain materials over time, which may require costly replacements for certain textiles, soft goods, and interior materials, particularly plastics.

SUMMARY OF THE DISCLOSURE

A need exists for a system and a method for disinfecting surfaces of structures and components that can be safely operated in the presence of humans, and which does not degrade materials. Further, a need exists for a system and a method for efficiently and effectively neutralizing various microorganisms, such as bacteria and germs.

With those needs in mind, certain embodiments of the present disclosure provide a sanitizing system configured to disinfect at least one surface within an area. The sanitizing system includes a lighting assembly configured to emit a disinfecting visible light onto the at least one surface. The disinfecting visible light is configured to neutralize microorganisms on the at least one surface. In at least one embodiment, the disinfecting visible light has a wavelength between 400 nm-410 nm. For example, the disinfecting visible light has a wavelength of 405 nm. In at least one embodiment, the lighting assembly is configured to continuously emit the disinfecting visible light. In at least one embodiment, the area may be an enclosed space, such as within a vehicle, including aircraft, rail vehicles, marine and submarines vehicles, space vehicles, and the like.

In at least one embodiment, a lighting control unit is in communication with the lighting assembly. The lighting control unit is configured to operate the lighting assembly to emit the disinfecting visible light.

For example, the lighting control unit is configured to operate the lighting assembly in a first mode and a second mode. The disinfecting visible light is emitted at a first intensity in the first mode. The the disinfecting visible light is emitted at a second intensity that differs from the first intensity in the second mode. As a further example, the lighting control unit is configured to operate the lighting assembly in a third mode. The disinfecting visible light is emitted at a third intensity in the third mode. The third intensity differs from the first intensity and the second intensity.

In at least one embodiment, one or more presence sensors are in communication with the lighting control unit. The one or more presence sensors are configured to detect a presence of an individual within the area and output presence signals to the lighting control unit. The lighting control unit selectively switches the lighting assembly between different modes based on the presence signals received from the presence sensors.

In at least one embodiment, a sensor is configured to determine when a toilet is flushed. The sensor is in communication with the lighting control unit. The lighting control unit selectively switches the lighting assembly between different modes in response to the toilet being flushed.

In at least one embodiment, a door has a lock. The lighting control unit is in communication with the lock (for example, a switch of the lock). The lighting control unit selectively switches the lighting assembly between different modes in response to the door being locked or unlocked.

As an example, the lighting assembly includes a first set of visible light emitting elements. The first set of visible light emitting elements is configured to emit white light (which includes an embedded disinfectant spectral content). The lighting assembly also includes a second set of visible light emitting elements. The second set of visible light emitting elements is configured to emit the disinfecting visible light (which may include little spectral content outside of the disinfecting spectra).

Certain embodiments of the present disclosure provide a sanitizing method configured to disinfect at least one surface within an area. The sanitizing method includes emitting, by a lighting assembly, disinfecting visible light onto the at least one surface, wherein the disinfecting visible light is configured to neutralize (for example, incapacitate or destroy) microorganisms on the at least one surface. In at least one embodiment, said emitting includes continuously emitting the disinfecting visible light.

In at least one embodiment, the sanitizing method further comprises communicatively coupling a lighting control unit with the lighting assembly, and operating, by the lighting control unit, the lighting assembly. For example, said operating includes operating the lighting assembly in a first mode and a second mode, wherein the disinfecting visible light is emitted at a first intensity in the first mode, and wherein the disinfecting visible light is emitted at a second intensity that differs from the first intensity in the second mode. As a further example, said operating also includes operating the lighting assembly in a third mode, wherein the disinfecting visible light is emitted at a third intensity in the third mode, and wherein the third intensity differs from the first intensity and the second intensity.

In at least one embodiment, the sanitizing method includes communicatively coupling one or more presence sensors with the lighting control unit, detecting, by the one or more presence sensors, a presence of an individual within the area, outputting, by the one or more presence sensors, presence signals to the lighting control unit, and selectively switching, by the lighting control unit, the lighting assembly between different modes based on the presence signals received from the presence sensors.

In at least one example, the sanitizing method includes selectively switching, by the lighting control unit, the lighting assembly between different modes in response to a toilet being flushed.

In at least one embodiment, the sanitizing method includes selectively switching, by the lighting control unit, the lighting assembly between different modes in response to a door being locked or unlocked.

Certain embodiments of the present disclosure provide a vehicle including an internal cabin defining at least one area, and a sanitizing system configured to disinfect at least one surface within the at least one area, as described herein.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system that includes a light assembly that emits disinfecting visible light, which effectively deactivates microorganisms, such as bacteria, germs, and viruses, while being safe for human exposure. The disinfecting visible light has a wavelength that is within the light spectrum that is visible to humans. In at least one embodiment, the disinfecting visible light has a wavelength between 400 nm-425 nm. For example, it has been found that disinfecting visible light having a wavelength of 405 nm effectively deactivates various microorganisms, such as certain bacteria, germs, and viruses. As described herein, embodiments of the present disclosure provide systems and methods that emit visible light to sanitize surfaces of structures and components.

Embodiments of the present disclosure provide visible light disinfection systems and methods that allow for continuous (that is, without interruption) emission of disinfecting visible light, such as within an internal cabin of a vehicle. In at least one embodiment, the systems and methods do not emit ultraviolet light, and are therefore safer for use in the presence of humans. Visible light disinfection, in conjunction with occupancy sensors, may operate based on different modes such that when an enclosed space is unoccupied, the light assembly can boost the disinfecting visible light to a higher dose. The disinfecting visible light can be continuously emitted from the light assembly, thereby preventing, minimizing, or otherwise reducing an overall presence of various microorganisms, such as certain bacteria, germs, and viruses.

In at least one embodiment, the lighting assembly can be selectively operated based on phases of a trip (such as a flight). For example, the lighting assembly can continuously emit the disinfecting visible light while selectively switching among different lighting schemes within an enclosed space, such as a galley, a lavatory, a cargo hold, a flight deck, a crew rest space, and/or the like. The lighting assemblies may be disposed through an internal cabin of a vehicle, for example. With the addition of visible light disinfection light emitters (such as light emitting diodes, bulbs, lamps, or the like), the lighting assembly can be selectively switched between various lighting modes, each of which may continuously emit the disinfecting visible light.

In at least one embodiment, the disinfecting visible light can be emitted in a low intensity mode when individuals are present, and a high intensity mode when individuals are not present. For example, the high intensity mode is safe for use in the presence of individuals, but the resulting light may not be aesthetically pleasing and/or amenable to reading, for example. A lighting control unit can automatically control the lighting assembly based on predetermined criteria. Additionally or optionally, the lighting assembly can be manually controlled. For example, the lighting control unit can be in communication with one or more presence sensors that are configured to detect presence of an individual within an enclosed space. The lighting control unit can selectively switch the lighting assembly between different modes based on whether or not an individual is within the enclosed space.

In at least one embodiment, the lighting assembly may be used within a lavatory. The lighting control unit is in communication with the lighting assembly, a sensor for detecting a toilet flush, and a sensor for detecting if a door has been opened. The lighting control unit monitors the sensors and based on sensing the flush and/or the door opening (such as indicating an individual is no longer within the lavatory), increasing an intensity of the disinfecting visible light to efficiently disinfect surfaces within the lavatory. In contrast, when the sensors indicate that an individual is within the lavatory, the lighting control unit decreases the intensity of the disinfecting light and may increase intensity of warm or cool white light, which provides a more aesthetically desirable illumination within the lavatory.

As described herein, embodiments of the present disclosure provide systems and methods for disinfecting surfaces within an enclosed space, such as within an internal cabin of a vehicle. The lighting assembly may continuously emit the disinfecting visible light, instead of periodic emission of disinfecting light (as is the case with ultraviolet systems and methods). As such, embodiments of the present disclosure provide systems and methods that continuously and automatically sanitize surfaces within an enclosed space.

As described herein, a sanitizing system is configured to disinfect at least one surface within an enclosed space. The sanitizing system includes a lighting assembly is configured to emit disinfecting visible light (in contrast to UV light) onto the at least one surface. The disinfecting visible light is configured to neutralize (for example, render inactive, kill, minimize, or otherwise reduce) microorganisms on the at least one surface.

Figures 1A, 1B:
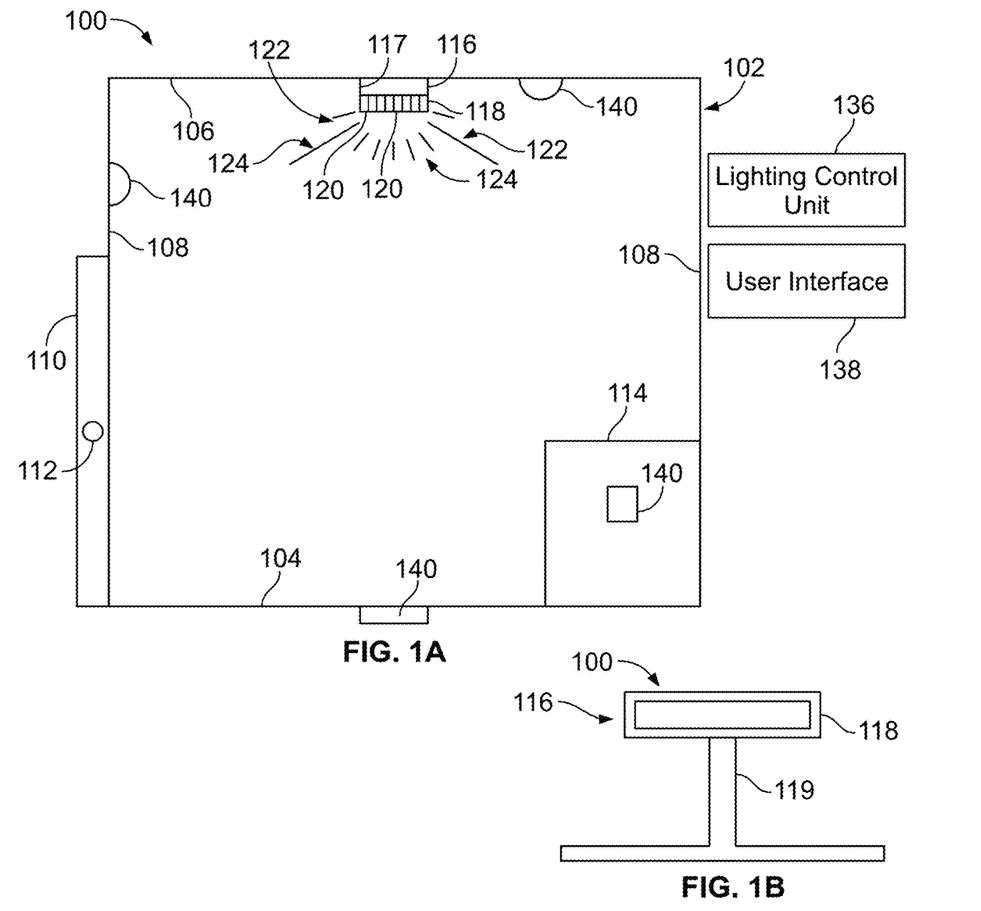
FIG. 1A illustrates a schematic diagram of a visible light sanitizing system for an enclosed space, according to an embodiment of the present disclosure.
FIG. 1B illustrates a schematic diagram of visible light sanitizing system for an area, according to an embodiment of the present disclosure.

FIG. 1A illustrates a schematic diagram of visible light sanitizing system 100 for an area, such as an enclosed space 102, according to an embodiment of the present disclosure. The visible light sanitizing system 100 may be used in various areas, whether enclosed, partially enclosed, or open. In at least one embodiment, the enclosed space may not be in direct sunlight.

The enclosed space 102 may be defined by a floor 104, a ceiling 106, and walls 108 extending between the floor 104 and the ceiling 106. A door 110 may be moveably secured to one of the walls 108. The door 110 includes a lock 112 that is configured to securely lock the door 110 in a closed position. When the lock 112 is in a locked position, the door 110 is unable to be opened. When the lock 112 is in an unlocked position, the door 110 may be opened. The enclosed space 102 may be a confined space onboard a commercial aircraft. For example, the enclosed space 102 may be a lavatory onboard an aircraft. As another example, the enclosed space 102 may be a galley onboard an aircraft. As yet another example, the enclosed space 102 may be a passenger cabin onboard an aircraft. The enclosed space 102 may or may not include the door 110. The enclosed space 102 may be within various other vehicles, structures, and/or the like. For example, the enclosed space 102 may be a room within a commercial, municipal, or residential building, or a room onboard a train, bus, ship, or the like.

The enclosed space 102 includes at least one structure 114 to be sanitized (for example, disinfected, sterilized, or otherwise cleaned) after use. For example, the structure 114 may be one or more of a toilet, sink, floor, countertop, cabinet, and/or the like within a lavatory of an aircraft.

The visible light sanitizing system 100 includes a lighting assembly 116 that includes a housing 117 and visible light emitter 118. The lighting assembly 116 is mounted to a portion of the enclosed space 102, such as through the housing 117. For example, the lighting assembly 116 can be mounted the ceiling 106. As another example, the lighting assembly 116 can be mounted to a wall 108 or the floor 104. In at least one embodiment, multiple lighting assemblies 116 are disposed within the enclosed space 102.

In at least one embodiment, the visible light emitter 118 includes one or more visible light elements 120, such as a lamp(s), light emitting diode(s) (LEDs), microfilament(s), fiber optic element(s), bulb(s), and/or the like. The visible light emitter 118 is configured to emit visible light 122, which includes disinfecting visible light 124.

In at least one embodiment, the disinfecting visible light 124 has a wavelength of between 400 nm-425 nm. As a more particular example, the disinfecting visible light 124 has a wavelength of between 400 nm-410 nm. In at least one embodiment, the disinfecting visible light 124 has a wavelength of 405 nm. It has been found that the disinfecting visible light 124 having a wavelength of 405 nm effectively neutralizes various microorganisms, such as certain bacteria, germs, and viruses. For example, visible light having a wavelength of 405 nm excites porphyrin in cells of certain microorganisms. With continued exposure to the visible light at a wavelength of 405 nm, the porphyrin becomes overly excited and damaged, thereby rendering the cells inactive due to an oxygen dependent reaction within the cells. Notably, the cell membranes experience oxygenated damage, and therefore the cells are unable to function. The lighting assembly 116 continuously emits the disinfecting visible light 124, thereby ensuring that microorganisms on surfaces within the enclosed space that are exposed to the disinfecting visible light 124 are rendered inactive. As such, the lighting assembly 116 effectively and efficiently sanitizes surfaces within the enclosed space 102.

Figure 2:
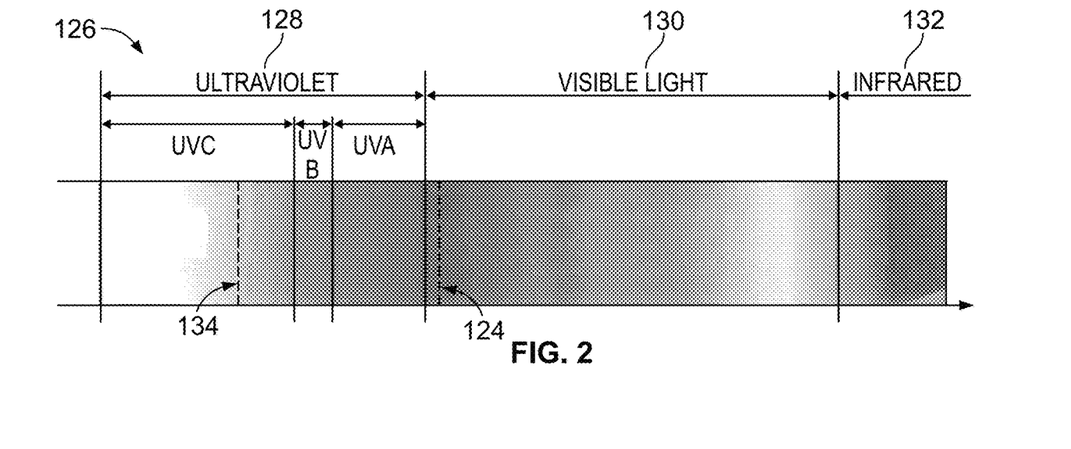
FIG. 2 illustrates a light spectrum.

FIG. 2 illustrates a light spectrum 126. The light spectrum 126 includes ultraviolet light 128, visible light 130, and infrared light 132. The visible light 130 includes the disinfecting visible light 124, such as indigo light at 405 nm, in contrast to typical UVC germicidal light 134, such as having a wavelength of 254 nm or 265 nm. The disinfecting visible light 124, such as indigo light at 405 nm, is safe in relation to humans. That is, humans can safely be exposed to indigo light at 405 nm. As such, the disinfecting visible light 124 can continuously be emitted by the lighting assembly 116 (shown in FIG. 1A) even when individuals are in the enclosed space 102. In contrast, UV sanitizing systems typically emit UVC germicidal light 134 intermittently, such as when there are no individuals within the enclosed space 102. However, in contrast to the continuous emission of the disinfecting visible light 124, intermittent UVC germicidal light 134 allows microorganisms to activate and/or multiply when the UVC germicidal light 134 is not emitted.

Referring again to FIG. 1A, a lighting control unit 136 is in communication with the lighting assembly 116, such as through one or more wired or wireless connections. The lighting control unit 136 may be positioned within or connected to the enclosed space 102, or may be remotely located therefrom. In at least one embodiment, the lighting control unit 136 is housed within the lighting assembly 116. The lighting control unit 136 is configured to control operation of the lighting assembly 116, such as to selectively switch between different lighting modes, all of which may emit the disinfecting visible light 124. In at least one embodiment, the lighting control unit 136 can utilize a firmware profile that includes various kinds profiles loaded thereon, such as via a wireless upload.

In at least one embodiment, the lighting control unit 136 is configured to operate the lighting assembly 116 in a first mode and a second mode. The disinfecting visible light 124 is emitted at a first intensity in the first mode, and the disinfecting visible light 124 is emitted at a second intensity that differs from the first intensity in the second mode. For example, the second intensity may be greater than the first intensity. In at least one embodiment, the second intensity is at least four times the first intensity. Further, the lighting control unit 136 may be further configured to operate the lighting assembly 116 in a third mode. The disinfecting visible light 124 is emitted at a third intensity in the third mode. The third intensity differs from the first intensity and the second intensity. For example, the third intensity may be greater than the first intensity, but less than the second intensity.

A user interface 138, such as a computer station, a portable computer, a handheld device (for example, a smart phone or smart tablet), and/or the like, may be in communication with the lighting control unit 136, such as through one or more wired or wireless connections. The user interface 138 allows an individual to selectively control the lighting assembly 116. For example, the user interface 138 allows the individual to manually turn the lighting assembly 116 on and off, select between different modes, and/or the like. Optionally, the visible light sanitizing system 100 may not include the user interface 138.

In at least one embodiment, operational architecture for the visible light sanitizing system 100 may be coordinated, synchronized, or the like with that of a vehicle, such as an aircraft. For example, when an aircraft reaches a cruising altitude, for example, a signal, such as sent from a control unit, from a wheel-up command to the lighting control unit 136 to automatically operate the lighting assembly 116 at a first setting. As another example, during descent, a signal is sent to the lighting control unit 136 to automatically operate the lighting assembly 116 at a second setting, such as at an intensified disinfecting mode (for example, a lavatory is unoccupied during a descent), and may revert back to the first setting when the aircraft parks at a gate.

One or more presence sensors 140 may be secured within the enclosed space 102. The presence sensors 140 may be ultrasound sensors, infrared sensors, thermal sensors, and/or the like that are configured to detect the presence of an individual within the enclosed space. In at least one embodiment, at least one presence sensor 140 (such as coupled to the floor 104) may be a digital scale that detects the presence of an individual through a discernable detection of mass or weight within the enclosed space 102. The presence sensors 140 are in communication with the lighting control unit 136 through one or more wired or wireless connections. Based on presence signals received from the presence sensors 140, the lighting control unit 136 determines whether or not an individual is within the enclosed space 102. In at least one embodiment, the lighting control unit 136 operates the lighting assembly 116 to emit the visible light 122 in different modes based on whether or not an individual is within the enclosed space 102.

For example, based on the presence signals as received from the presence sensors 140, when the lighting control unit 136 determines that an individual is within the enclosed space 102, the lighting control unit 136 operates the lighting assembly 116 in a first mode (such as a standard illumination mode), in which the visible light emitter 118 emits the visible light 122 as white light, which includes the disinfecting visible light 124 (such as having a wavelength of 405 nm). By emitting the white light that includes the disinfecting visible light 124, familiar white light illuminates the enclosed space 102, and the disinfecting visible light 124 may not be discernable to an individual within the enclosed space 102. In this manner, the disinfecting visible light 124 is continuously emitted to disinfect surfaces within the enclosed space 102, and familiar, aesthetically desirable white light illuminates the enclosed space 102.

When the presence sensors 140 emit presence signals that indicate that no individual is present within the enclosed space 102, the lighting control unit 136 can operate the lighting assembly 116 in a second mode that differs from the first mode. For example, the second mode can be a deep clean mode, in which the disinfecting visible light 124 is emitted at an increased intensity or power. For example, in the deep clean mode, lighting assembly 116 can emit the disinfecting visible light 124 having a wavelength of 405 nm at four times an intensity as compared to the first mode. In the second mode, the lighting assembly 116 may or may not emit white light. As such, power to the lighting assembly 116 can be diverted to one or more portions of the visible light emitter 118 that emit the disinfecting visible light 124, and away from one or more portions that emit visible light at other wavelengths. In this manner, power consumed by the lighting assembly 116 may be redistributed, instead of increased.

While the disinfecting visible light 124 in the second mode is emitted at an increased intensity, the disinfecting visible light 124 is safe for human exposure. However, the disinfecting visible light 124 may be viewed by individuals as aesthetically undesirable, and may therefore not be emitted when an individual is within the enclosed space 102.

The lighting assembly 116 can also be operated by the lighting control unit 136 in a third mode, such as a white plus increased disinfecting mode. Such may be used when an individual is within the enclosed space 102. Such mode includes white light (which includes at least a portion of the disinfecting visible light 124) and increased disinfecting visible light 124, such as at an increased intensity. For example, certain light emitting elements may be dedicated disinfecting visible light emitters. In this manner, white light can be emitted, along with disinfecting visible light 124 at an increased intensity. The additional disinfecting visible light 124 may darken the overall illumination, which may be used such to provide reading illumination and increased disinfection. For example, the third mode may be used within an internal cabin during night time, when certain passengers are asleep.

As used herein, the terms first, second, third, and the like are merely for labeling purposes. For example, the first mode may optionally be the second or third mode, the second mode may optionally be the first or third mode, and the third mode may optionally be the first or second mode.

The user interface 138 may be used to selectively switch the lighting assembly 116 between the different modes. As another example, the lighting control unit 136 automatically switches the lighting assembly between the different modes, such as based on the presence of one or more individuals within the enclosed space 102 (such as an internal cabin of a vehicle), a time of day, a phase of travel (such as takeoff, cruising, and landing of a commercial aircraft), and/or the like.

As another example, the structure 114 can include a sensor 140. For example, the structure 114 may be a toilet, and the sensor 140 is configured to determine when the toilet is flushed. For example, the sensor 140 can be an audio sensor, a fluid flow sensor, a pressure sensor, and/or the like. The lighting control unit 136 is in communication with the flush sensor, and may selectively switch between modes based on when the toilet is flushed. For example, the lighting control unit 136 can switch the lighting assembly 116 to a deep clean mode a predetermined period, such as one minute, after the toilet has been flushed and/or presence sensors 140 detect an individual is no longer within the enclosed space 102.

As another example, the lighting control unit 136 may be configured to determine that the enclosed space is unoccupied, such as by being in communication with the lock 112. For example, the lighting control unit 136 may determine that the enclosed space 102 is unoccupied when the door 110 is locked. When the door 110 is locked, the lighting control unit 136 may operate the lighting assembly 116 only in a standard illumination mode, for example, such as described herein. As another example, the lighting control unit 136 may switch to a second mode (for example, the deep clean mode) based on a sequence of events, which may be triggered by the structure 114 being used, the door 110 being unlocked, and the door 110 being subsequently closed.

FIG. 1B illustrates a schematic diagram of visible light sanitizing system for an area, according to an embodiment of the present disclosure. In this embodiment, the lighting assembly 116 including the visible light emitter 118 may be supported on a stand 119, for example. The stand 119 may include one or more moveable portions. For example, the lighting assembly 116 may be a lamp that is configured to be supported on a surface, such as a desk, cabinet, floor, or the like. As another example, the lighting assembly 116 may be part of a handheld system. For example, the lighting assembly 116 may be included in a wand.

Figure 3:
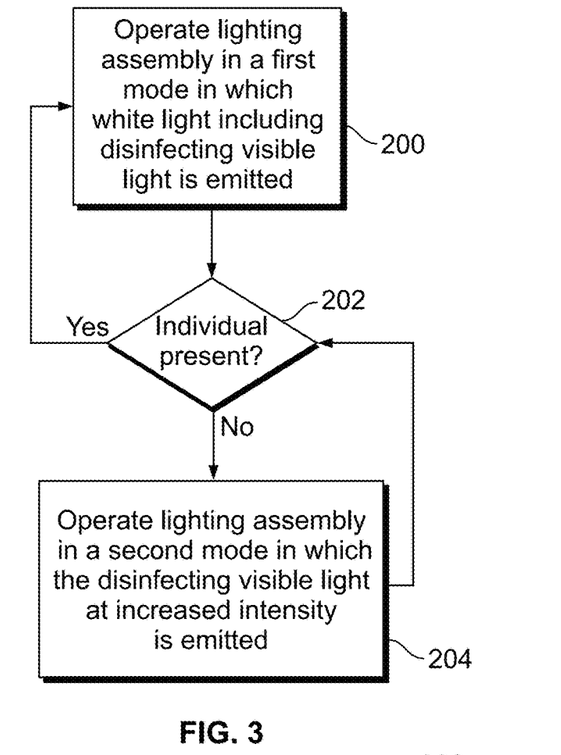
FIG. 3 illustrates a flow chart of a visible light sanitizing method for an enclosed space, according to an embodiment of the present disclosure.

FIG. 3 illustrates a flow chart of a visible light sanitizing method for an enclosed space, according to an embodiment of the present disclosure. Referring to FIGS. 1A, 1B, and 3, at 200, the lighting control unit 136 operates the lighting assembly 116 in a first mode, in which white light including the disinfecting visible light 124 is emitted. At 202, the lighting control unit 136 determines if one or more individuals are present within the enclosed space, such as through one or more presence sensors 140 and/or the lock 112, as described herein. If an individual is present, the method returns to 200. If, however, an individual is not present, the method proceeds from 202 to 204, at which the lighting control unit 136 operates the lighting assembly 116 in a second mode, in which the disinfecting visible light 124 at an increased intensity (such as four times the intensity as in the first mode) is emitted. In the second mode, the white light may or may not also be emitted. The method then returns to 202. The visible light sanitizing method may also include a third mode, in which white light (which includes at least a portion of a disinfecting visible light) is emitted, along with additional emitted disinfecting visible light.

In at least one other embodiment, instead of (or optionally in addition to) detecting whether or not an individual is present at 202, the method may include operate based on a timer, program, or response to various types of sensors, microphones, or the like. For example, after a predetermined period of time, the lighting assembly may switch modes. As another example, the lighting assembly may switch between modes based on an audio command, such as voice through a microphone.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the lighting control unit 136 may be or include one or more processors that are configured to control operation of the lighting assembly 116, as described above.

The lighting control unit 136 is configured to execute a set of instructions that are stored in one or more data storage units or elements (such as one or more memories), in order to process data. For example, the lighting control unit 136 may include or be coupled to one or more memories. The data storage units may also store data or other information as desired or needed. The data storage units may be in the form of an information source or a physical memory element within a processing machine.

The set of instructions may include various commands that instruct the lighting control unit 136 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the lighting control unit 136. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the lighting control unit 136 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 4:
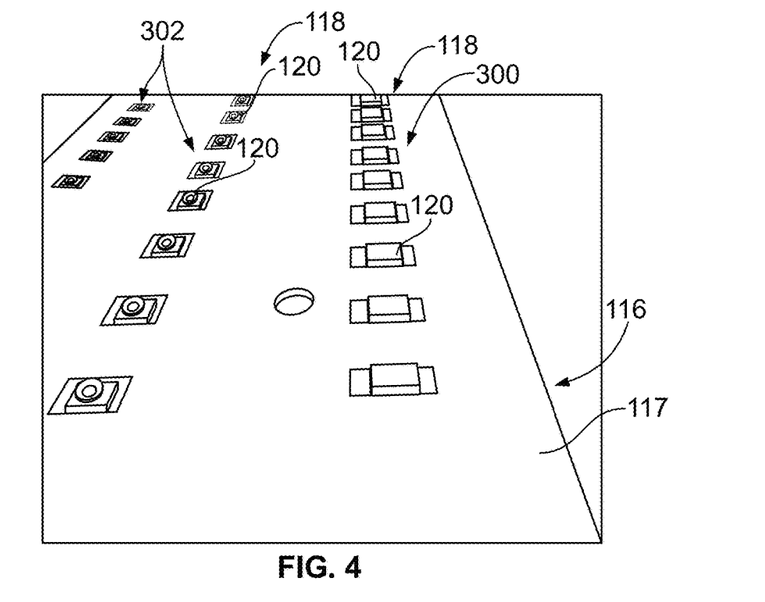
FIG. 4 illustrates a perspective bottom view of a lighting assembly, according to an embodiment of the present disclosure.

FIG. 4 illustrates a perspective bottom view of the lighting assembly 116, according to an embodiment of the present disclosure. In at least one embodiment, the visible light emitter 118 includes a first set of visible light emitting elements 300 (such as light emitting diodes (LEDs), and a second set of visible light emitting elements 302 (such as LEDs). The visible light emitting elements 300 are configured to emit light at a first wavelength range, and the visible light emitting elements 302 are configured to emit light at a second wavelength range that differs from the first wavelength range. For example, the first wavelength range may be a white light range. As such, the visible light emitting elements 300 are configured to emit white light. The second wavelength range may be a disinfecting visible light range, such as between 400 nm-410 nm. As such, the visible light emitting elements 302 are dedicated to emitting solely the disinfecting visible light, while the visible light emitting elements 300 emit a wider range of visible light, which may also include the disinfecting visible light.

As shown, the visible light emitting elements 300 and 302 may be arranged in rows or columns. As another option, the visible light emitting elements 300 may be clustered in a first group, while the visible light emitting elements 302 may be closeted in a second group. As another example, the visible light emitting elements 300 may be interspersed between or otherwise among the visible light emitting elements 302 (such as alternately between different elements).

Figure 5:
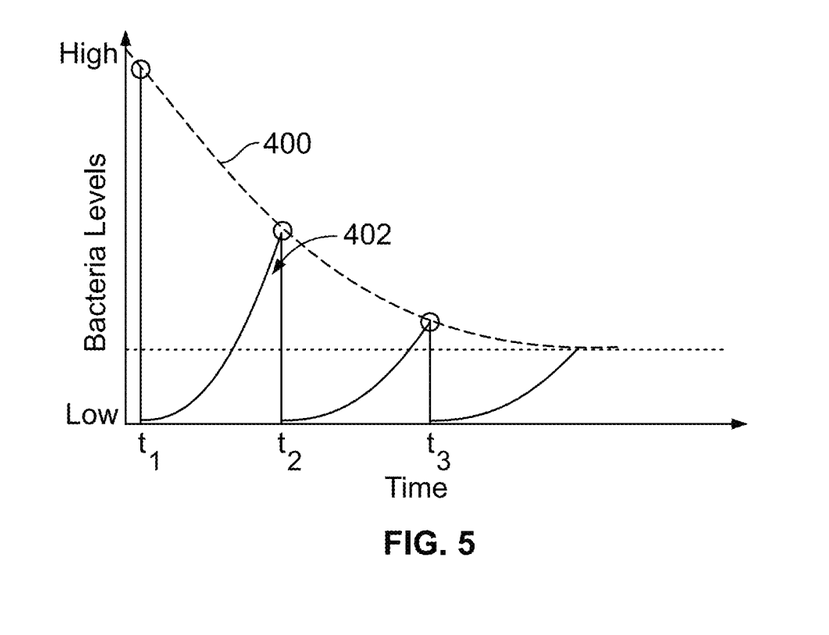
FIG. 5 illustrates a graph of bacteria levels with respect to time in relation to continuous emission of disinfecting visible light.

FIG. 5 illustrates a graph of bacteria levels with respect to time in relation to continuous emission of disinfecting visible light. A continuous light emission curve 400 shows that continuous emission of the disinfecting visible light steadily, effectively, and efficiently reduces bacteria levels over time. In contrast, an episodic emission of UV light, as presented by pattern 402, shows that while the UV light may quickly reduce bacteria, because the UV light is intermittently (that is, episodically) emitted, the bacteria regrow until the UV light is emitted at times t1, t2, and t3.

Figure 6:
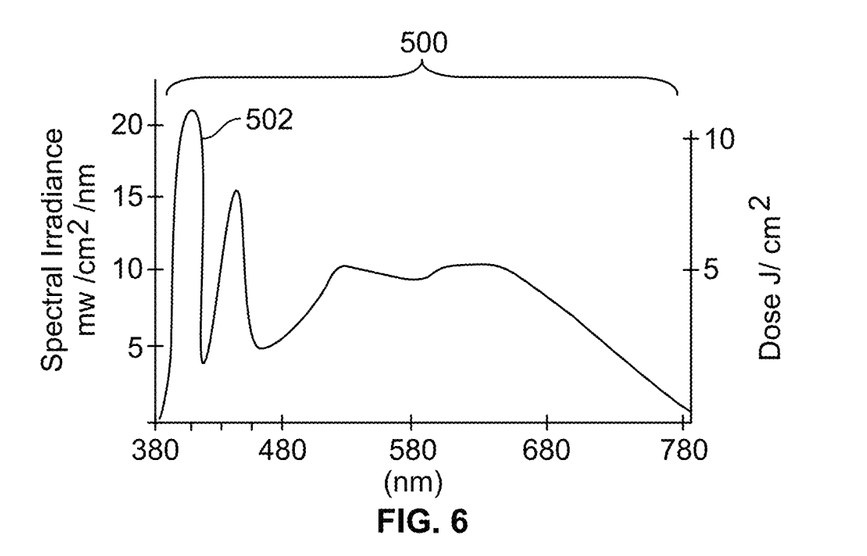
FIG. 6 illustrates a spectral irradiance graph of a standard illumination mode, according to an embodiment of the present disclosure.

FIG. 6 illustrates a spectral irradiance graph of a standard illumination mode (for example, a first mode), according to an embodiment of the present disclosure. The standard illumination mode is configured for use when individuals are present. Referring to FIGS. 1A, 1B, and 6, the lighting control unit 136 operates the lighting assembly 116 in the standard illumination mode when the lighting control unit 136 determines that an individual is present within the enclosed space 102. As shown, white light 500 is emitted during the standard illumination mode. The white light 500 includes the disinfecting visible light 124 having a first intensity 502. In the standard illumination mode, 6500 K white LEDs, 405 nm LEDs, and 2800 K white LEDs may be activated to emit the visible light shown.

Figure 7:
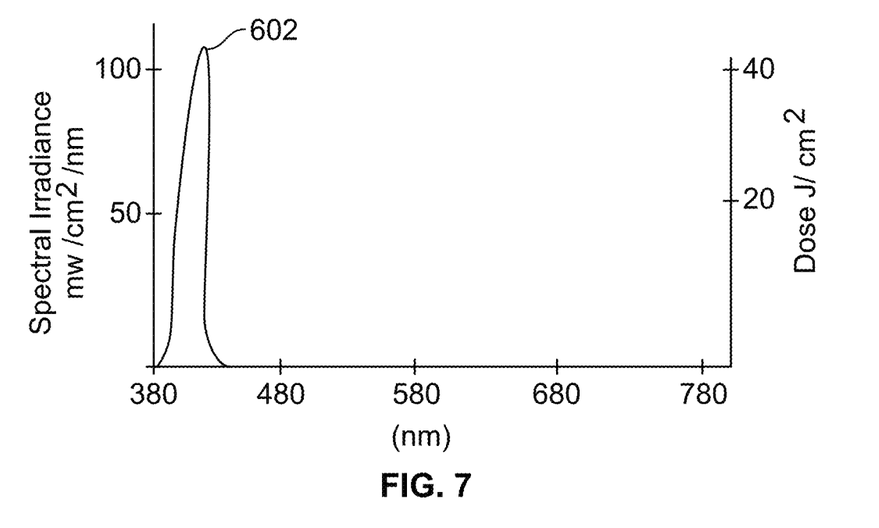
FIG. 7 illustrates a spectral irradiance graph of an increased disinfecting mode, according to an embodiment of the present disclosure.

FIG. 7 illustrates a spectral irradiance graph of an increased disinfecting mode (for example, a second mode), according to an embodiment of the present disclosure. The increased disinfecting mode is configured for use when individuals are not present. Referring to FIGS. 1A, 1B, and 7, in the increased disinfecting mode, white light is not emitted. Instead, only the disinfecting visible light 124 is emitted. The disinfecting visible light 124 can be emitted at an increased second intensity 602 as compared to the first intensity 502 (shown in FIG. 6). For example, the second intensity 602 can be four to five times the first intensity. In the increased disinfecting mode, only 405 nm LEDs may be activated to emit the visible light shown.

Figure 8:
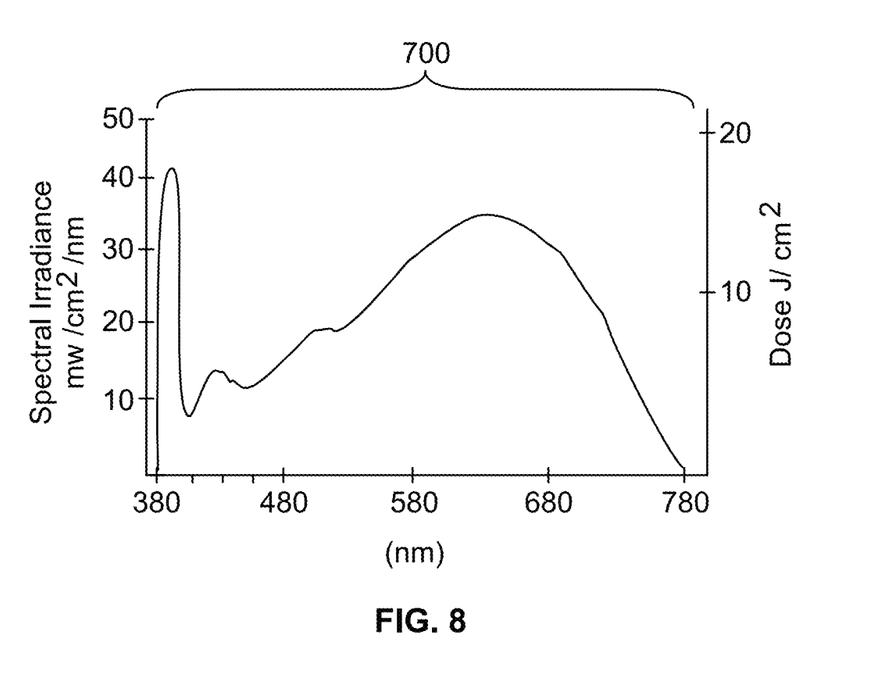
FIG. 8 illustrates a spectral irradiance graph of a night light mode, according to an embodiment of the present disclosure.

FIG. 8 illustrates a spectral irradiance graph of a night light mode (for example, a third mode), according to an embodiment of the present disclosure. Referring to FIGS. 1A, 1B, and 8, the night light mode redistributes power among the white light 700, as compared to the white light 500 shown in FIG. 6. Further, the disinfecting visible light 124 can be emitted at an increased third intensity 702 (as compared to the first intensity 502 shown in FIG. 6). For example, the third intensity 702 can be twice the first intensity 502. In the night light mode, the 405 nm LEDs and the 6500K or 2800 K white LEDs may be activated to emit the light shown.

In at least one embodiment, an additional mode includes a 222 nm UVC LED, which may be activated to deliver a quick deactivating disinfectant dose during unoccupied states in a lavatory (such as 60 seconds or less), which may quickly (such as within 5 seconds) follow opening of the latch or lock (which indicates an unoccupied state). Such a disinfecting mode is well suited for cargo holds or other areas that are typically unoccupied.

Referring to FIGS. 1-8, the visible light sanitizing systems and methods are particularly well-suited and useful for areas in which individuals are frequently present and moving, such as within internal cabins of vehicles. The disinfecting visible light 124 is safe for skin and eyes (at exposures of less than 2.8 continuous hours for adults staring uninterrupted at the source, and a 0.5 hours of continuous exposure for children staring uninterrupted at the source), and can be continuously emitted to reduce microorganisms in the absence of individuals. The lighting control unit 136 can automatically operate the lighting assembly 116, as described. In contrast to UV lights, for example, the lighting assembly 116 that emits visible light is less costly, and requires little to no maintenance.

Figure 9:
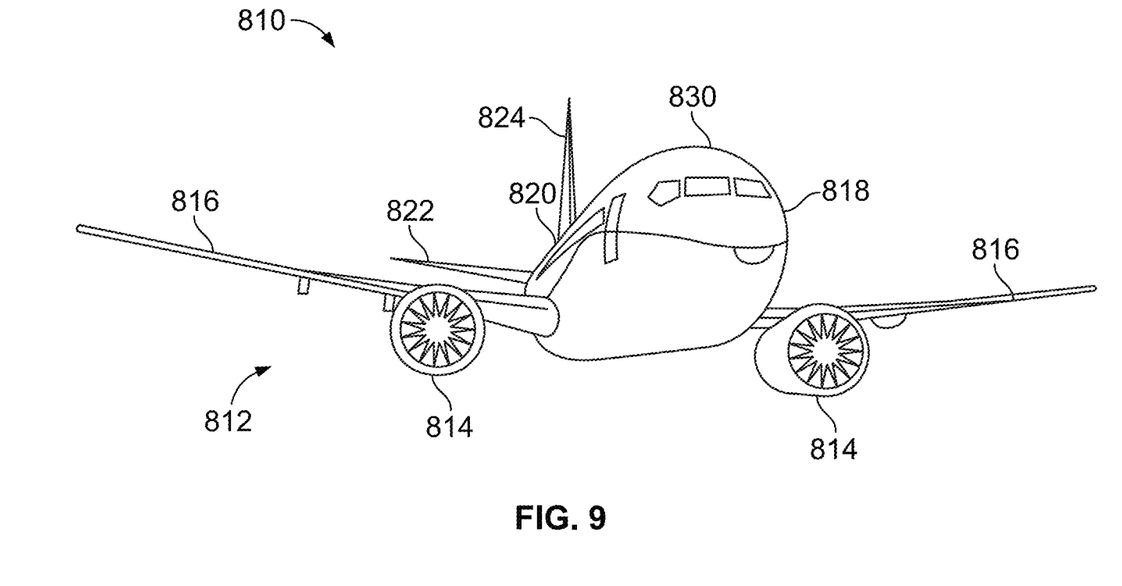
FIG. 9 illustrates a perspective front view of an aircraft, according to an embodiment of the present disclosure.

FIG. 9 illustrates a perspective front view of an aircraft 810, according to an embodiment of the present disclosure. The aircraft 810 includes a propulsion system 812 that includes engines 814, for example. Optionally, the propulsion system 812 may include more engines 814 than shown. The engines 814 are carried by wings 816 of the aircraft 810. In other embodiments, the engines 814 may be carried by a fuselage 818 and/or an empennage 820. The empennage 820 may also support horizontal stabilizers 822 and a vertical stabilizer 824.

The fuselage 818 of the aircraft 810 defines an internal cabin 830, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 830 is an example of, or otherwise includes, an enclosed space, such as the enclosed space 102 shown in FIG. 1A.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 10A:
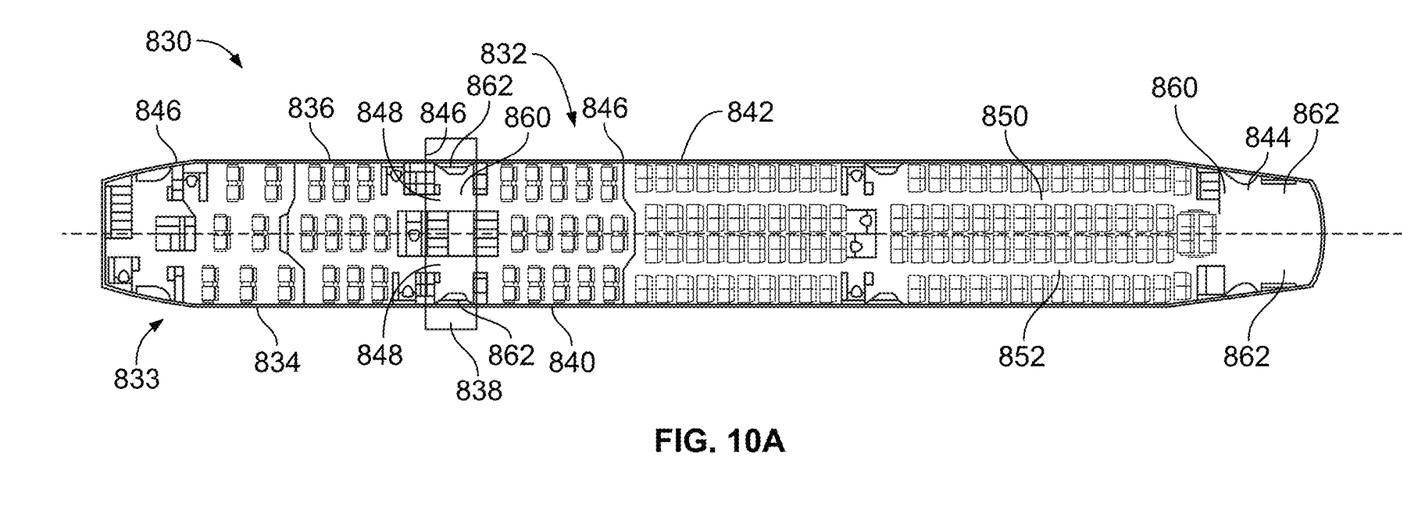
FIG. 10A illustrates a top plan view of an internal cabin of an aircraft, according to an embodiment of the present disclosure.

FIG. 10A illustrates a top plan view of an internal cabin 830 of an aircraft, according to an embodiment of the present disclosure. The internal cabin 830 may be within the fuselage 832 of the aircraft, such as the fuselage 818 of FIG. 9. For example, one or more fuselage walls may define the internal cabin 830. The internal cabin 830 includes multiple sections, including a front section 833, a first class section 834, a business class section 836, a front galley station 838, an expanded economy or coach section 840, a standard economy of coach section 842, and an aft section 844, which may include multiple lavatories and galley stations. It is to be understood that the internal cabin 830 may include more or less sections than shown. For example, the internal cabin 830 may not include a first class section, and may include more or less galley stations than shown. Each of the sections may be separated by a cabin transition area 846, which may include class divider assemblies between aisles 848.

As shown in FIG. 10A, the internal cabin 830 includes two aisles 850 and 852 that lead to the aft section 844. Optionally, the internal cabin 830 may have less or more aisles than shown. For example, the internal cabin 830 may include a single aisle that extends through the center of the internal cabin 830 that leads to the aft section 844.

The aisles 848, 850, and 852 extend to egress paths or door passageways 860. Exit doors 862 are located at ends of the egress paths 860. The egress paths 860 may be perpendicular to the aisles 848, 850, and 852. The internal cabin 830 may include more egress paths 860 at different locations than shown. One or more lighting assemblies 116, as shown in FIG. 1A, are disposed within the internal cabin 830. The lighting assemblies 116 may be used to sanitize (with disinfecting visible light) various structures within the internal cabin 830, such as passenger seats, monuments, stowage bin assemblies, components on and within lavatories, galley equipment and components, and/or the like.

Figure 10B:
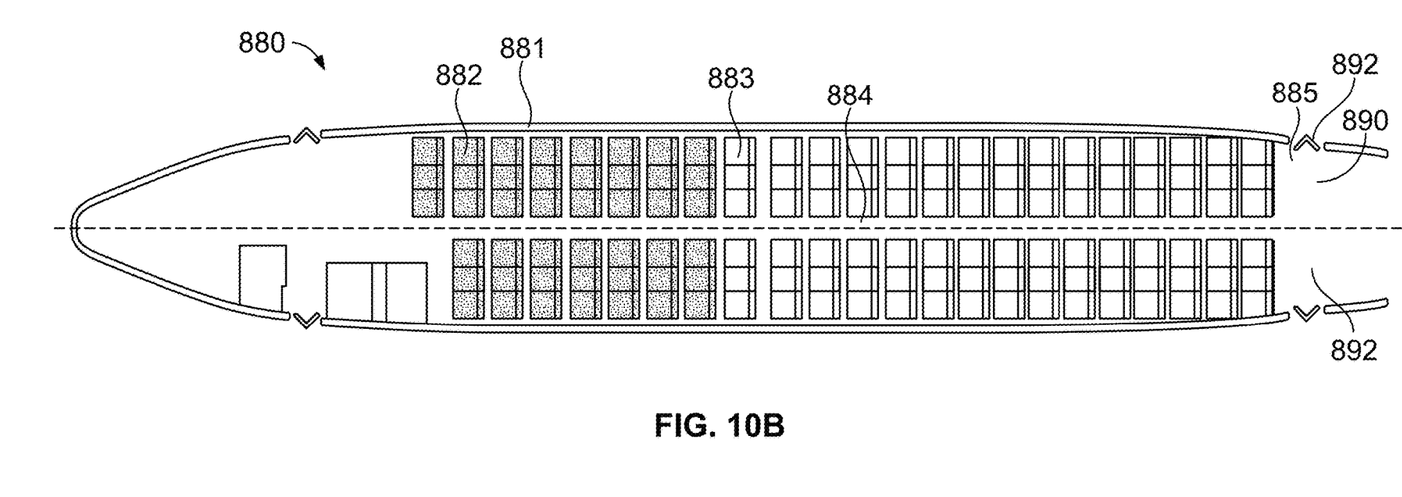
FIG. 10B illustrates a top plan view of an internal cabin of an aircraft, according to an embodiment of the present disclosure.

FIG. 10B illustrates a top plan view of an internal cabin 880 of an aircraft, according to an embodiment of the present disclosure. The internal cabin 880 is an example of the internal cabin 830 shown in FIG. 9. The internal cabin 880 may be within a fuselage 881 of the aircraft. For example, one or more fuselage walls may define the internal cabin 880. The internal cabin 880 includes multiple sections, including a main cabin 882 having passenger seats 883, and an aft section 885 behind the main cabin 882. It is to be understood that the internal cabin 880 may include more or less sections than shown.

The internal cabin 880 may include a single aisle 884 that leads to the aft section 885. The single aisle 884 may extend through the center of the internal cabin 880 that leads to the aft section 885. For example, the single aisle 884 may be coaxially aligned with a central longitudinal plane of the internal cabin 880.

The aisle 884 extends to an egress path or door passageway 890. Exit doors 892 are located at ends of the egress path 890. The egress path 890 may be perpendicular to the aisle 884. The internal cabin 880 may include more egress paths than shown. One or more lighting assemblies 116, as shown in FIG. 1A, are disposed within the internal cabin 880. The lighting assemblies 116 may be used to sanitize (with disinfecting visible light) various structures within the internal cabin 880, such as passenger seats, monuments, sidewalls proximate to where passengers were previously sitting, stowage bin assemblies, entryways, crew spaces and berths, cargo areas, components on and within lavatories, galley equipment and components, and/or the like.

Figure 11:
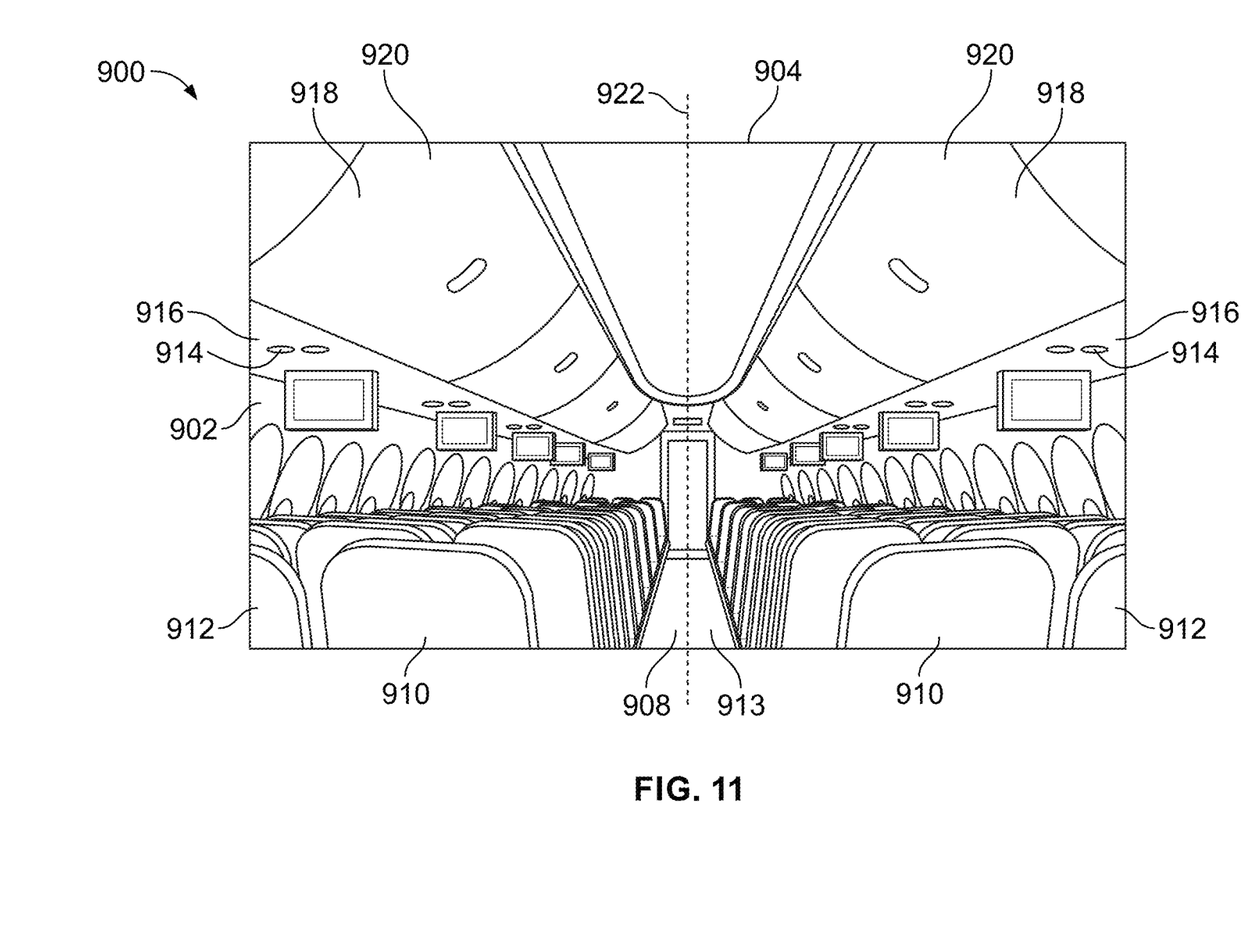
FIG. 11 illustrates a perspective interior view of an internal cabin of an aircraft, according to an embodiment of the present disclosure.

FIG. 11 illustrates a perspective interior view of an internal cabin 900 of an aircraft, according to an embodiment of the present disclosure. The internal cabin 900 includes outboard walls 902 connected to a ceiling 904. Windows 306 may be formed within the outboard walls 902. A floor 908 supports rows of seats 910. As shown in FIG. 11, a row 912 may include two seats 910 on either side of an aisle 913. However, the row 912 may include more or less seats 910 than shown. Additionally, the internal cabin 900 may include more aisles than shown.

Passenger service units (PSUs) 914 are secured between an outboard wall 902 and the ceiling 904 on either side of the aisle 913. The PSUs 914 extend between a front end and rear end of the internal cabin 900. For example, a PSU 914 may be positioned over each seat 910 within a row 912. Each PSU 914 may include a housing 916 that generally contains vents, reading lights, an oxygen bag drop panel, an attendant request button, and other such controls over each seat 910 (or groups of seats) within a row 912.

Overhead stowage bin assemblies 918 are secured to the ceiling 904 and/or the outboard wall 902 above and inboard from the PSU 914 on either side of the aisle 913. The overhead stowage bin assemblies 918 are secured over the seats 910. The overhead stowage bin assemblies 918 extend between the front and rear end of the internal cabin 900. Each stowage bin assembly 918 may include a pivot bin or bucket 920 pivotally secured to a strongback (hidden from view in FIG. 11). The overhead stowage bin assemblies 918 may be positioned above and inboard from lower surfaces of the PSUs 914. The overhead stowage bin assemblies 918 are configured to be pivoted open in order to receive passenger carry-on baggage and personal items, for example.

As used herein, the term "outboard" means a position that is further away from a central longitudinal plane 922 of the internal cabin 900 as compared to another component. The term "inboard" means a position that is closer to the central longitudinal plane 922 of the internal cabin 900 as compared to another component. For example, a lower surface of a PSU 914 may be outboard in relation to a stowage bin assembly 918.

One or more lighting assemblies 116, as shown in FIG. 1A, are disposed within the internal cabin 900. The lighting assemblies 116 may be used to sanitize (with disinfecting visible light) various structures within the internal cabin 900, such as passenger seats, monuments, stowage bin assemblies, components on and within lavatories, galley equipment and components, and/or the like.

Figure 12:
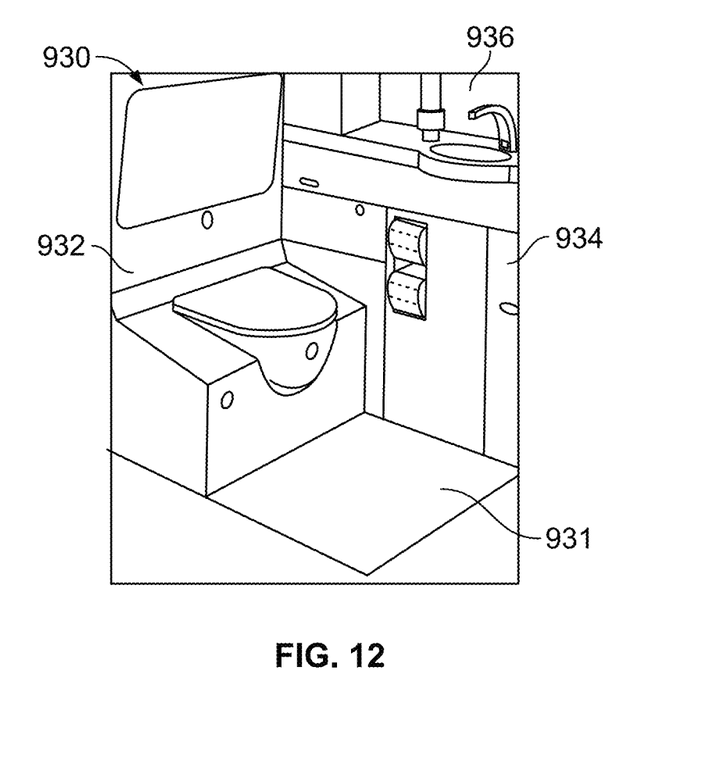
FIG. 12 illustrates a perspective internal view of a lavatory within an internal cabin of an aircraft.

FIG. 12 illustrates a perspective internal view of a lavatory 930 within an internal cabin of a vehicle, such as any of the internal cabins described herein. The lavatory 930 is an example of an enclosed space, monument or chamber, such as within the internal cabin a vehicle. The lavatory 930 may be onboard an aircraft, as described above. Optionally, the lavatory 930 may be onboard various other vehicles. In other embodiments, the lavatory 930 may be within a fixed structure, such as a commercial or residential building. The lavatory 930 includes a base floor 931 that supports a toilet 932, cabinets 934, and a sink 936 or wash basin. The lavatory 930 may be arranged differently than shown. The lavatory 930 may include more or less components than shown. One or more lighting assemblies 116, as shown in FIG. 1A, are disposed within the lavatory 930. The lighting assemblies 116 may be used to sanitize (with disinfecting visible light) various structures within the lavatory 930, such as the base floor 931, the toilet 932, the cabinets 934, the sink 936, and the like.

As described herein, embodiments of the present disclosure provide systems and methods for disinfecting surfaces of structures and components that can be safely operated in the presence of humans. Further, embodiments of the present disclosure provide systems and methods for safely, efficiently, and effectively neutralizing various microorganisms, such as bacteria and germs.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing system configured to disinfect at least one surface within an area, the sanitizing system comprising:
    a lighting assembly configured to emit a disinfecting visible light onto the at least one surface, wherein the disinfecting visible light is configured to neutralize microorganisms on the at least one surface;
    a lighting control unit in communication with the lighting assembly, wherein the lighting control unit is configured to operate the lighting assembly to emit the disinfecting visible light; and
    a sensor configured to determine when a toilet is flushed, wherein the sensor is in communication with the lighting control unit, wherein the lighting control unit is configured to selectively switch the lighting assembly between different modes in response to the toilet being flushed, and wherein the lighting assembly in each of the different modes is configured to emit the disinfecting light.

2. The sanitizing system of claim 1, wherein the disinfecting visible light has a wavelength between 400 nm-410 nm.

3. The sanitizing system of claim 1, wherein the disinfecting visible light has a wavelength of 405 nm.

4. The sanitizing system of claim 1, wherein the lighting assembly is configured to continuously emit the disinfecting visible light.

5. The sanitizing system of claim 1, wherein the area is an enclosed space within a vehicle.

6. The sanitizing system of claim 1, wherein the lighting control unit is configured to operate the lighting assembly in a first mode and a second mode, wherein the disinfecting visible light is emitted at a first intensity in the first mode, and wherein the disinfecting visible light is emitted at a second intensity that differs from the first intensity in the second mode.

7. The sanitizing system of claim 6, wherein the lighting control unit is further configured to operate the lighting assembly in a third mode, wherein the disinfecting visible light is emitted at a third intensity in the third mode, and wherein the third intensity differs from the first intensity and the second intensity.

8. The sanitizing system of claim 1, further comprising one or more presence sensors in communication with the lighting control unit, wherein the one or more presence sensors are configured to detect a presence of an individual within the area and output presence signals to the lighting control unit, and wherein the lighting control unit selectively switches the lighting assembly between different modes based on the presence signals received from the presence sensors.

9. The sanitizing system of claim 1, further comprising a door having a lock, wherein the lighting control unit is in communication with the lock, and wherein the lighting control unit selectively switches the lighting assembly between different modes in response to the door being locked or unlocked.

10. The sanitizing system of claim 1, wherein the lighting assembly comprises:
    a first set of visible light emitting elements, wherein the first set of visible light emitting elements is configured to emit white light; and
    a second set of visible light emitting elements, wherein the second set of visible light emitting elements is configured to emit the disinfecting visible light.

11. The sanitizing system of claim 1, wherein the lighting control unit is configured to decrease an intensity of the disinfecting visible light in response to sensing an individual within the area.

12. The sanitizing system of claim 1, wherein the lighting control unit is configured to switch the lighting assembly to a deep clean mode a predetermined period after the toilet has been flushed.

13. The sanitizing system of claim 1, wherein the lighting control unit is configured to coordinate operation of the lighting assembly to emit the disinfecting visible light based on different phases of a trip of a vehicle.

14. A method for a sanitizing system configured to disinfect at least one surface within an area, the sanitizing system comprising:
    a lighting assembly configured to emit a disinfecting visible light onto the at least one surface, wherein the disinfecting visible light is configured to neutralize microorganisms on the at least one surface;
    a lighting control unit in communication with the lighting assembly, wherein the lighting control unit is configured to operate the lighting assembly to emit the disinfecting visible light; and a sensor configured to determine when a toilet is flushed, wherein the sensor is in communication with the lighting control unit, wherein the lighting control unit is configured to selectively switch the lighting assembly between different modes in response to the toilet being flushed, and wherein the lighting assembly in each of the different modes is configured to emit the disinfecting light, the method comprising:

communicatively coupling the lighting control unit with the lighting assembly;

emitting, by the lighting assembly, the disinfecting visible light; and selectively switching, by the lighting control unit, the lighting assembly between different modes in response to the toilet being flushed.

15. The method of claim 14, wherein the disinfecting visible light has a wavelength of 405 nm.

16. The method of claim 14, further comprising:

operating, by the lighting control unit, the lighting assembly, wherein said operating comprises operating the lighting assembly in a first mode and a second mode, wherein the disinfecting visible light is emitted at a first intensity in the first mode, and wherein the disinfecting visible light is emitted at a second intensity that differs from the first intensity in the second mode.

17. The method of claim 16, wherein said operating further comprises operating the lighting assembly in a third mode, wherein the disinfecting visible light is emitted at a third intensity in the third mode, and wherein the third intensity differs from the first intensity and the second intensity.

18. The method of claim 16, further comprising:

communicatively coupling one or more presence sensors with the lighting control unit;

detecting, by the one or more presence sensors, a presence of an individual within the area;

outputting, by the one or more presence sensors, presence signals to the lighting control unit; and selectively switching, by the lighting control unit, the lighting assembly between different modes based on the presence signals received from the presence sensors.

19. The method of claim 16, further comprising selectively switching, by the lighting control unit, the lighting assembly between different modes in response to a door being locked or unlocked.

20. A vehicle comprising:

an internal cabin defining at least one area; and a sanitizing system configured to disinfect at least one surface within the at least one area, the sanitizing system comprising:

a lighting assembly configured to continuously emit disinfecting visible light onto the at least one surface, wherein the disinfecting visible light is configured to neutralize microorganisms on the at least one surface, wherein the disinfecting visible light has a wavelength between 400 nm-410 nm; and a lighting control unit in communication with the lighting assembly, wherein the lighting control unit is configured to operate the lighting assembly to emit the disinfecting visible light, wherein the lighting control unit is configured to operate the lighting assembly in a first mode and a second mode, wherein the lighting assembly in each of the first mode and the second mode is configured to emit the disinfecting light, wherein the disinfecting visible light is emitted at a first intensity in the first mode, and wherein the disinfecting visible light is emitted at a second intensity that differs from the first intensity in the second mode, and wherein the lighting control unit is configured to coordinate operation of the lighting assembly to emit the disinfecting visible light based on different phases of a trip of a vehicle.

* * * * *